US00PP12023P2

(12) United States Plant Patent
VandenBerg

(10) Patent No.: US PP12,023 P2
(45) Date of Patent: Jul. 31, 2001

(54) CHRYSANTHEMUM PLANT NAMED 'YORENO'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/383,539

(22) Filed: Aug. 26, 1999

(51) Int. Cl.[7] ..... A01H 5/00
(52) U.S. Cl. ..... Plt./296
(58) Field of Search ..... Plt./286, 296

*Primary Examiner*—Howard J. Locker
(74) *Attorney, Agent, or Firm*—C. A. Whealy

(57) ABSTRACT

A distinct cultivar of Chrysanthemum plant named 'Yoreno', characterized by its upright, outwardly spreading and uniformly mounded plant habit; vigorous and strong growth habit; freely branching habit; strong, dark green foliage; uniform flowering; nine-week response time; numerous large daisy-type inflorescences that are about 7.5 cm in diameter; dark orange-colored ray florets that doesn't fade; ray florets held upright; large disc with dark green disc florets that are slow to mature to bright yellow; good postproduction longevity with inflorescences and leaves maintaining good substance and color for about two to three weeks in an interior environment; and excellent year-round production performance.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yoreno.

The new Chrysanthemum is a product of a planned breeding program conducted by the Inventor in Salinas, Calif. The objective of the breeding program is to create new pot-type Chrysanthemum cultivars having desirable inflorescence forms and floret colors and good post-production longevity.

The new Chrysanthemum originated from a cross made by the Inventor in October, 1994, in Salinas, Calif., of the *Dendranthema grandiflora* cultivar Rage, disclosed in U.S. Plant Pat. No. 8,770, as the female, or seed, parent, with the *Dendranthema grandiflora* cultivar Miramar, disclosed in U.S. Plant Pat. No. 7,469, as the male, or pollen, parent.

The new Chrysanthemum was discovered and selected by the Inventor as a flowering plant within the progeny of the stated cross in a controlled environment in Alva, Fla., in November, 1995. The selection of this plant was based on its desirable inflorescence form and floret colors and good post-production longevity.

Asexual reproduction of the new Chrysanthemum by terminal cuttings harvested in a controlled environment in Alva, Fla., has shown that the unique features of this new Chrysanthemum are stable and reproduced true to type in successive generations.

SUMMARY OF THE INVENTION

The cultivar Yoreno has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoreno'.

These characteristics in combination distinguish 'Yoreno' as a new and distinct Chrysanthemum:

1. Upright, outwardly spreading and uniformly mounded plant habit.
2. Vigorous and strong growth habit.
3. Freely branching habit, full and dense plants.
4. Strong, dark green foliage.
5. Uniform flowering.
6. Nine-week response time.
7. Freely flowering; numerous large daisy-type inflorescences that are about 7.5 cm in diameter.
8. Dark orange-colored ray florets that resist fading; ray florets held upright.
9. Large disc with green disc florets that are slow to mature to bright yellow.
10. Good postproduction longevity with inflorescences and leaves maintaining good substance and color for about two to three weeks in an interior environment.
11. Excellent year-round production performance.

The new Chrysanthemum can be compared to the Chrysanthemum cultivar Orange Davis, disclosed in U.S. Plant Pat. No. 8,295. However in side-by-side comparisons in Salinas, Calif., and Leamington, Ontario, Canada, under commercial practice, plants of the new Chrysanthemum differ from plants of the cultivar Orange Davis in the following characteristics:

1. Plants of the new Chrysanthemum are stronger than plants of the cultivar Orange Davis.
2. Plants of the new Chrysanthemum are typically not as outwardly spreading as plants of the cultivar Orange Davis.
3. Plants of the new Chrysanthemum are more freely branching, fuller and denser than plants of the cultivar Orange Davis.
4. Plants of the new Chrysanthemum have shorter leaves than plants of the culltivar Orange Davis.
5. Inflorescences of plants of the new Chrysanthemum are larger and have more ray florets than inflorescences of plants of the cultivar Orange Davis.

6. Inflorescences of plants of the new Chrysanthemum have darker orange, longer, and narrower ray florets than inflorescences of plants of the cultivar Orange Davis.
7. Spray formation of plants of the new Chrysanthemum is not as clubby as spray formation of plants of the cultivar Orange Davis.
8. Plants of the new Chrysanthemum have much better winter production performance than plants of the cultivar Orange Davis.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Yoreno'.

The photograph at the bottom of the first sheet comprises a close-up view of a typical inflorescence and upper (left) and lower (right) surfaces of typical leaves of the cultivar Yoreno.

The photograph at the top of the second sheet comprises a side perspective view of typical flowering plants of 'Yoreno' (left) and 'Orange Davis' (right).

The photograph at the bottom of the second sheet comprises a close-up view of typical inflorescences of plants of 'Yoreno' (left) and 'Orange Davis' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Plants used for this description were grown as spray-types. Measurements and numerical values represent averages of typical flowering plants.

Botanical classification: *Dendranthema grandiflora* cultivar Yoreno.

Commercial classification: Daisy spray-type pot Chrysanthemum.

Parentage:

*Female or seed parent.*—*Dendranthema grandiflora* cultivar Rage, disclosed in U.S. Plant Pat. No. 8,770.

*Male or pollen parent.*—*Dendranthema grandiflora* cultivar Miramar, disclosed in U.S. Plant Pat. No. 7,469.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy pot Chrysanthemum typically grown as a spray-type. Inverted triangle; compact; upright and outwardly spreading giving a uniformly mounded appearance to the plant. Vigorous and strong plants. Freely branching; about five lateral branches develop after removal of terminal apex (pinching); dense and full plants. Strong stems.

*Plant height.*—About 25.5 cm.

*Plant width.*—About 39 cm.

*Stem color.*—146A.

*Stem texture.*—Pubescent.

*Foliage description.*—Arrangement: Alternate. Length: About 7.1 cm. Width: About 5 cm. Apex: Mucronate. Base: Mostly truncate. Margin: Palmately lobed, sinuses between lateral lobes mostly parallel. Texture: Upper and lower surfaces with very fine pubescence; veins prominent on lower surface. Petiole length: About 2.7 cm. Petiole diameter: About 3 mm. Color: Young foliage upper surface: 147A. Young foliage lower surface: 147B. Mature foliage upper surface: Close to 147A. Mature foliage lower surface: 147B. Venation upper surface: Close to 147A. Venation lower surface: 147B.

Inflorescence description:

*Appearance.*—Daisy inflorescence form with elongated-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about nine weeks later.

*Postproduction longevity.*—Inflorescences and leaves will maintain good color and substance for about two to three weeks in an interior environment.

*Quantity of Inflorescences.*—Freely flowering; about five inflorescences per lateral branch or about 25 inflorescences per plant.

*Inflorescence bud.*—Height: About 7 mm. Diameter: About 8 mm. Color: Darker than 143A.

*Inflorescence size.*—Diameter: About 7.5 cm. Depth (height): About 2.75 cm. Diameter of disc: About 1.7 cm.

*Ray florets.*—Shape: Elongated. Orientation: Mostly upright, about 135° to peduncle. Aspect: Flat. Length: About 4.1 cm. Width: About 7 mm. Apex: Rounded or emarginate. Margin: Entire. Texture: Smooth, velvety. Number of ray florets per inflorescence: About 57. Color: When opening: Close to 172A. Fully opened, upper surface: Close to 169A, slightly more red towards apex; base, yellow, 9A; corolla tube, white. Fully opened, lower surface: 169A, overlaid with tan, 168C–168D; yellow, 9A, towards base.

*Disc florets.*—Shape: Tubular. Apex: Serrated. Length: About 8 mm. Width: Apex, about 1.5 mm; base, about 1 mm. Number of disc florets per inflorescence: Numerous, about 148. Color: Immature: 154A; slow to mature, green color is maintained for a long time. Mature: Apex: 9A. Mid-section: Very light greenish white. Base: White, 155D.

*Reproductive organs.*—Androecium: Present on disc florets only. Anther color: 9A. Pollen amount: Moderate. Pollen color: 17A. Gynoecium: Present on both ray and disc florets.

Disease resistance: Resistance to pathogens common to Chrysanthemums has not been observed on plants grown under commercial greenhouse conditions.

Seed productions: Seed production has not been observed.

It is claimed:

1. A new and distinct cultivar of Chrysanthemum plant named 'Yoreno', as illustrated and described.

* * * * *

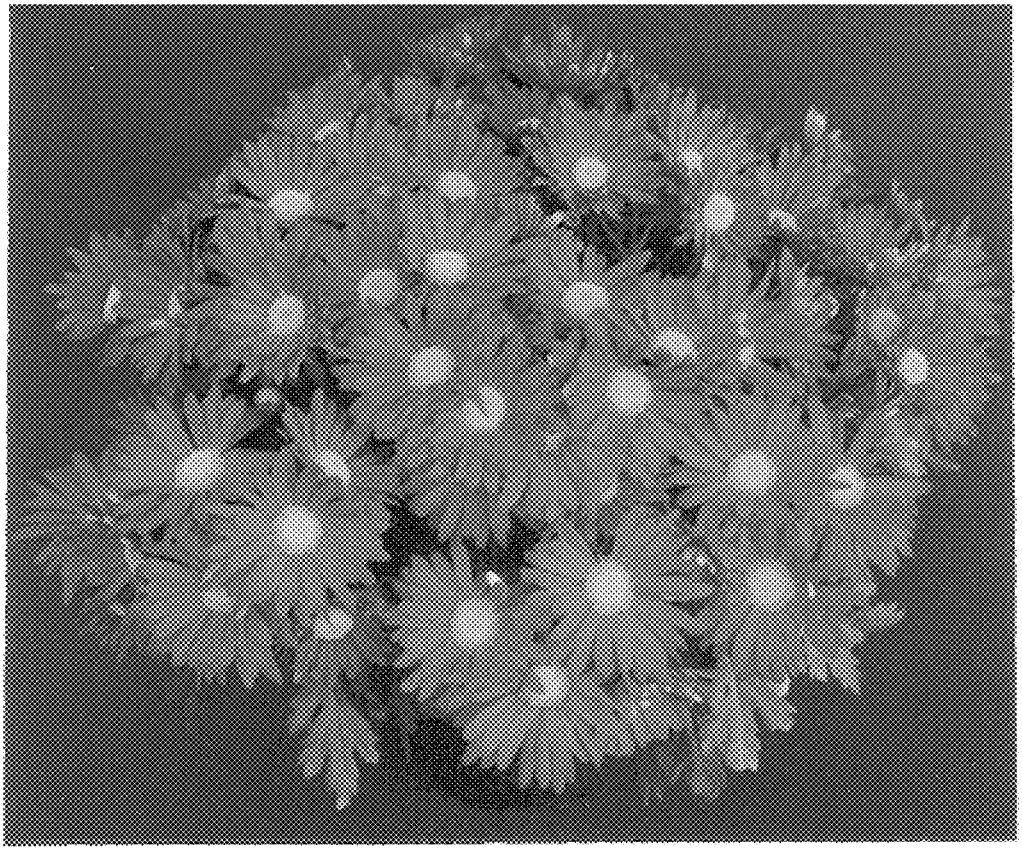
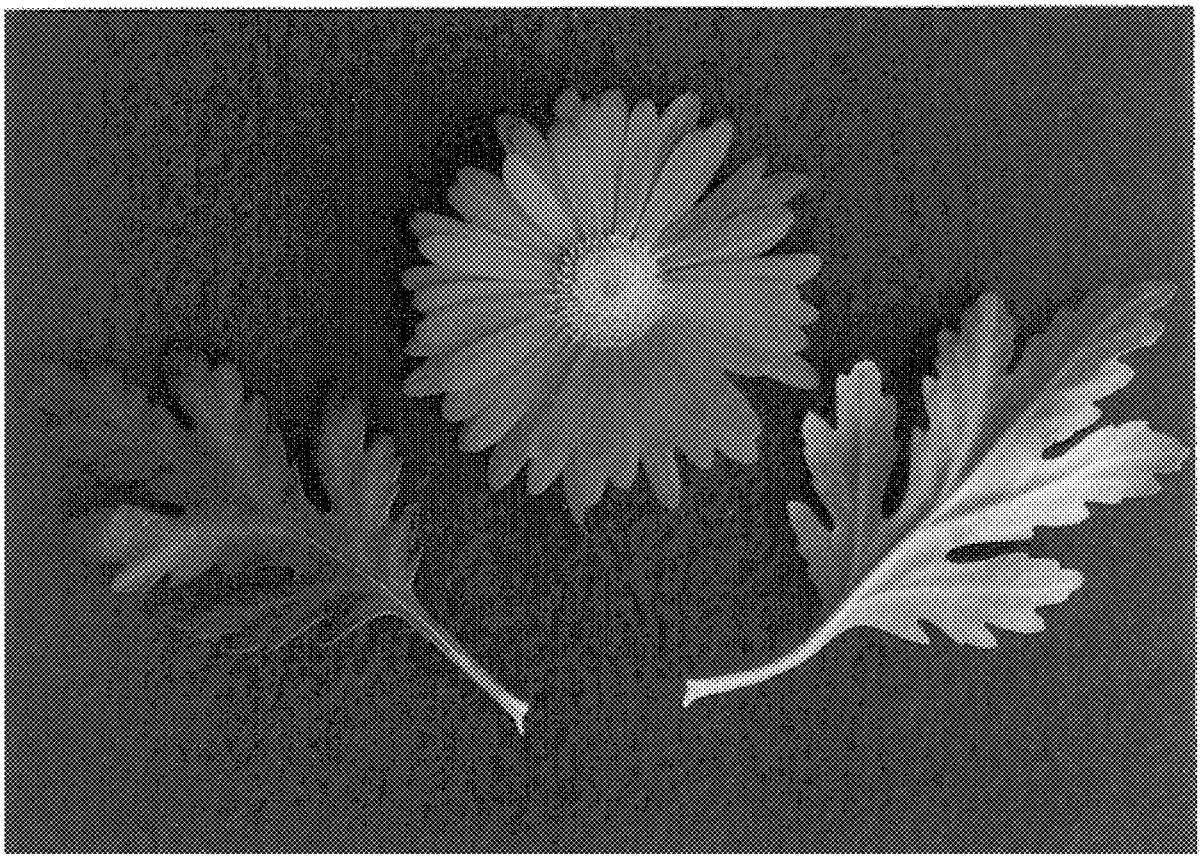

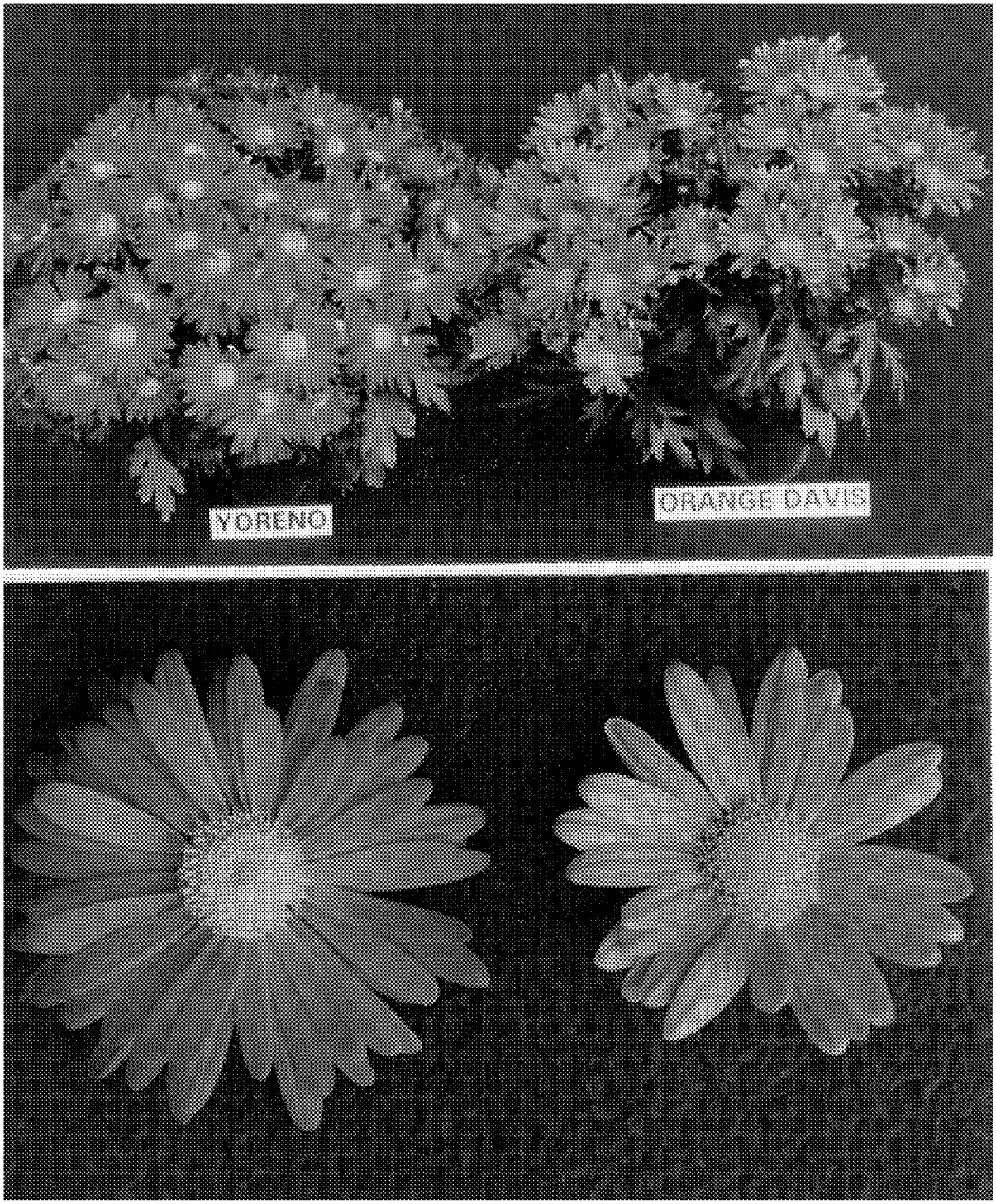
YORENO
ORANGE DAVIS